US007919499B2

(12) United States Patent
Ehrich (10) Patent No.: US 7,919,499 B2
(45) Date of Patent: Apr. 5, 2011

(54) NALTREXONE LONG ACTING FORMULATIONS AND METHODS OF USE

(75) Inventor: Elliot Ehrich, Lincoln, MA (US)

(73) Assignee: Alkermes, Inc., Waltham, MA (US)

( * ) Notice: Subject to any disclaimer, the term of this patent is extended or adjusted under 35 U.S.C. 154(b) by 1673 days.

(21) Appl. No.: 11/083,167

(22) Filed: Mar. 17, 2005

(65) Prior Publication Data

US 2005/0245558 A1   Nov. 3, 2005

Related U.S. Application Data

(60) Provisional application No. 60/564,542, filed on Apr. 22, 2004.

(51) Int. Cl.
*A61K 31/44* (2006.01)
*A61K 31/56* (2006.01)
*A01N 43/42* (2006.01)
*A01N 45/00* (2006.01)
*A61F 13/00* (2006.01)

(52) U.S. Cl. .................. 514/282; 514/171; 424/422
(58) Field of Classification Search .................. 514/282, 514/171; 424/422
See application file for complete search history.

(56) References Cited

U.S. PATENT DOCUMENTS

| 4,719,219 | A | 1/1988 | Arvidsson et al. |
| 4,882,335 | A | 11/1989 | Sinclair |
| 5,407,609 | A | 4/1995 | Tice et al. |
| 5,512,593 | A | 4/1996 | Dante |
| 5,654,008 | A | 8/1997 | Herbert et al. |
| 5,792,477 | A | 8/1998 | Rickey et al. |
| 6,143,314 | A * | 11/2000 | Chandrashekar et al. .... 424/426 |
| 6,264,987 | B1 | 7/2001 | Wright et al. |
| 6,306,425 | B1 | 10/2001 | Tice et al. |
| 6,358,443 | B1 | 3/2002 | Herbert et al. |
| 6,495,155 | B1 | 12/2002 | Tice et al. |
| 2004/0151774 | A1 | 8/2004 | Pauletti et al. |

FOREIGN PATENT DOCUMENTS

| WO | 01/15699 | 3/2001 |
| WO | 01/43726 A | 6/2001 |
| WO | WO 2004/064752 A2 | 8/2004 |
| WO | WO 2004/108084 A2 | 12/2004 |

OTHER PUBLICATIONS

O'Malley, Stephanie S. et al., "Initial and Maintenance Naltrexone Treatment for Alcohol Dependence Using Primary Care vs Specialty Care. A Nested Sequence of 3 Randomized Trials," Arch Intern Med., 163: 1695-1704 (2003).
Latt, Noeline C. et al., "Naltrexone in alcohol dependence: a randomised controlled trial of effectiveness in a standard clinical setting," MJA, 176: 530-534 (2002).
Heinala, Pekka et al., "Targeted Use of Naltrexone Without Prior Detoxification in the Treatment of Alcohol Dependence: A Factorial Double-Blind, Placebo-Controlled Trial," J Clinical Psychopharmacology, 21(3):287-292 (2001).
"Evidence for the Efficacy of Naltrexone in the Treatment of Alcohol Dependence (Alcoholism)," Addiction Treatment Forum, Ed., Leavitt, Stewart, pp. 1-8 (2002).
Reuning, R.H., et al., "Pharmacokinetic quantitation of naltrexone release from several sustained-released delivery," NIDA, Research Monograph, Institute on Drug Abuse, 28:172-184, (1981).
Yolles, S., et al., "Long acting delivery for narcotic antagonists II: release reates of naltrexone from Poly(lactic acid) composites," PDA J. of Pharm. Sci and Tech., 64(2):348-349, (1995).
Bartus, et al., Vivitrex®, an Injectable, Extended-Release Formulation of Naltrexone, Provides Pharmacokinetic and Pharmacodynamic Evidence of Efficacy for 1 Month in Rats, *Neuropsychopharmacology*, 28:1973-1982 (Aug. 2003).
Comer, Sandra D. et al., "Depot Naltrexone: Long-lasting Antagonism of the Effects of Heroin in Humans," Psychopharmacology, 159:351-360 (2002).
Chiang, C.N. et al., "Kinetics of a Naltrexone Sustained-release Preparation," Clinical Pharmacology and Therapeutics, 36(5): 704-708.
U.S. Appl. No. 60/554,658, filed Mar. 19, 2004, Elliott Ehrich, et al.
U.S. Appl. No. 60/554,785, filed Mar. 19, 2004, Elliott Ehrich, et al.
U.S. Appl. No. 11/082,420, filed Mar. 17, 2005, Elliott Ehrich, et al.
U.S. Appl. No. 11/082,534, filed Mar. 17, 2005, Elliott Ehrich, et al.
Swift, Robert M., "Drug Therapy for Alcohol Dependence," *New England J. of Med.*, 340(19): 1482-1490 (1999).
Karam-Hage, Maher and Brower, Kirk J., "Gabapentin Treatment for Insomnia Associated With Alcohol Dependence," *Am. J. Psychiatry*, 157(1): 151-153 (2000).
Myrick, M.D., Hugh, et al., "Gabapentin Treatment of Alcohol Withdrawal," *Am. J. of Psychiatry*, 155(11): 1626-1627, (1998).
Malcolm, M.D., Robert, et al., "Update on Anticonvulsants for the Treatment of Alcohol Withdrawal," *Am. J. on Addictions*, 10(1): 16-23, Abstract Only, (2001).
Swift, R., et al., "Naltrexone Effects on Diazepam Intoxication and Pharmacokinetics in Humans," *Psychopharmacology*, 135(3): 256-262 (1998), Abstract Only.
Chaves, M.L., et al., "Diazepam Inhibits Retroactive Interference of Memory in Humans: Pretreatment with Naltrexone Does Not Alter This Effect," *Braz. J. Med. Biol. Res.*, 23(5): 417-421 (1990), Abstract Only.
Fidecka, S. and Langwinski, R., "Effects of Opioid Antagonists on Anticonvulsant and Hypnotic Activity of Benzodiazepines," *Pol. J. Pharmacol.*, 48(4): 409-414 (1996), Abstract Only.
Longo, L.P., et al., "Divalproex Sodium (Depakote) for Alcohol Withdrawal and Relapse Prevention," *J. Addict Dis.*, 21(2): 55-64 (2002), Abstract Only.
Minuk, G.Y., et al., "The Use of Sodium Valproate in the Treatment of Alcoholism," *J. Addict Dis.*, 14(2): 67-74 (1995), Abstract Only.
Reoux, J.P., et al., "Divalproex Sodium in Alcohol Withdrawal: A Randomized Double Blind Placebo-Controlled Clinical Trial," *Alcohol Clin. Exp. Res.*, 25(9): 1324-1329 (2001), Abstract Only.

* cited by examiner

*Primary Examiner* — Sreeni Padmanabhan
*Assistant Examiner* — Kendra D Carter
(74) *Attorney, Agent, or Firm* — Elmore Patent Law Group, P.C.; Carolyn S. Elmore; Darlene A. Vanstone (57) ABSTRACT

The inventions described herein arose from unexpected discoveries made during clinical trials with a long acting formulation of naltrexone. As such, the invention includes a method for treating an individual in need of naltrexone comprising the step of parenterally administering a long acting formulation comprising naltrexone and to the use of naltrexone in the manufacture of medicaments for use in such methods.

15 Claims, 4 Drawing Sheets

NALTREXONE LONG ACTING FORMULATIONS AND METHODS OF USE

RELATED APPLICATION

This application claims the benefit of U.S. Provisional Application No. 60/564,542, filed on Apr. 22, 2004. The entire teachings of the above application are incorporated herein by reference.

BACKGROUND OF THE INVENTION

Alcohol dependence is a chronic disorder that results from a variety of genetic, psychological and environmental factors. Traditional treatment has consisted of two phases: detoxification and rehabilitation. Detoxification ameliorates the symptoms and signs of withdrawal; rehabilitation helps the patient avoid future problems with alcohol. In the past, most rehabilitative treatments have been psychosocial. With advances in neurobiology, there is increasing interest in drug therapy for alcohol dependence. For a discussion of the development of this field, see Swift, R., *Drug Therapy for Alcohol Dependence*, NEJM, May 13, 1999, 1482-1490. Yet, the successful treatment of alcoholism has many serious challenges and complications. Patient compliance is a serious problem.

Accordingly, there is a need for improving naltrexone therapies.

SUMMARY OF THE INVENTION

The inventions described herein arose from unexpected discoveries made during clinical trials with a long acting formulation of naltrexone. As such, the invention includes a method for treating an individual in need of naltrexone comprising the step of parenterally administering a long acting formulation comprising naltrexone to the individual wherein the serum AUC of naltrexone is at least about two times, preferably at least about three times, more preferably about 3.3 times greater over the course of the month than that achieved by 50 mg/day oral administration.

The inventions also include a method of treating an individual in need of naltrexone comprising administering a long acting formulation in a dose comprising at least about 160 mg of naltrexone, preferably between about 160 mg and about 480 mg naltrexone, more preferably between about 160 and 240 mg of naltrexone or about 310 to about 480 mg of naltrexone.

The inventions also include a method of treating an individual in need of naltrexone comprising administering naltrexone, such as in a long acting formulation, in the absence of co-administering alcohol, to an individual who has not abstained from alcohol within three days, such as five days, prior to the naltrexone administration.

The invention also includes a method of treating an individual in need of naltrexone comprising administering naltrexone as a long acting formulation in the absence of concomitant psychosocial treatment/intervention.

The inventions include a method of increasing the days prior to occurrence of alcohol consumption in an individual in need of naltrexone comprising administering a long acting formulation comprising naltrexone, in the absence of co-administering alcohol, to an individual who has not abstained from alcohol within three days, such as five days, prior to the naltrexone administration.

The inventions include a method of treating an individual in need of naltrexone comprising administering a long acting formulation comprising naltrexone in a dosage between about 160 mg to about 480 mg naltrexone every four weeks for a period of about 24 weeks or more wherein the individual has not used oral naltrexone within five days, such as within ten days, before said administration.

DETAILED DESCRIPTION OF THE INVENTION

The inventions relate to the administration of a naltrexone containing formulation, preferably a long acting naltrexone formulation, to patients in need thereof and to the use of naltrexone in the manufacture of medicaments for use in such methods.

In one embodiment, the invention includes a method for treating an individual in need of naltrexone comprising the step of parenterally administering a long acting formulation comprising naltrexone to the individual wherein the serum AUC of naltrexone is at least about two times, preferably at least about three times, more preferably about 3.3 times greater than that achieved by 50 mg/day oral administration. This invention arose from the unexpected discovery that substantially improved serum levels of naltrexone can be achieved by administering long acting formulations of naltrexone, such as the Alkermes, Inc. formulation, Vivitrex® injectable suspension, made employing its Medisorb® delivery system. Indeed, it was not expected that serum levels of about 3.3 times that achieved by a 50 mg/day oral dose could be achieved by a single IM administration of Vivitrex®.

The inventions also include a method of treating an individual in need of naltrexone comprising administering naltrexone, such as in a long acting formulation, in the absence of co-administering alcohol, to an individual who has not abstained from alcohol within three days, such as five days, prior to the naltrexone administration. In this embodiment, it was unexpectedly discovered that good to excellent results could be achieved without either requiring alcohol abstinence or requiring alcohol consumption during therapy, as taught by Sinclair, U.S. Pat. No. 4,882,335. Further, good to excellent results were achieved in patients that did not receive oral naltrexone in advance of the long acting formulation administration, contrary to the clinical protocols as taught by Drug Abuse Sciences. Thus, the inventions also include administering a long acting formulation to individuals who did not receive a prior oral dose of naltrexone, for example, within 3, such as within about 5 days or about 10 days of commencing therapy.

As such, the inventions also include a method of treating an individual in need of naltrexone comprising administering a long acting formulation in a dose comprising between about 160 mg and 240 mg of naltrexone or about 310 mg to about 480 mg of naltrexone and formulations for use in the methods described herein. Preferred formulations are administered in a dose comprising about 190 mg or about 380 mg naltrexone.

The naltrexone can be in any form, including anhydrous, hydrate, solvate or salt forms or combinations thereof. It can be crystalline or non-crystalline or combinations thereof. A preferred naltrexone form comprises a naltrexone ethanolate, such as that described in U.S. Patent Application No. 60/475,863, filed on Jun. 4, 2003, which is incorporated herein by reference and/or anhydrous naltrexone. A particularly preferred naltrexone form is that produced by the encapsulation process described in U.S. Pat. No. 6,264,987, by Wright et al., which is incorporated herein by reference.

The naltrexone can be combined with any of the well-known biodegradable and bioerodible carriers, such as polylactides, poly(lactic acids) and poly-lactide-co-glycolides and collagen formulations. A particularly preferred polymer is a polylactide-co-glycolide polymer which possesses a molecular weight of at least 100,000 daltons, such as those described below in the exemplification. Such materials may be in the form of solid implants, sponges, and the like.

As stated above, the naltrexone is preferably in a long acting formulation. Long acting (also referred to as extended, sustained, or controlled release) preparations may be achieved through the use of polymers (preferably poly-lactide or poly-lactide-co-glycolide polymers) to entrap or encapsulate the naltrexone described herein. Extended release formulations can be made by spray drying polymer-drug mixtures, emulsion-based technologies, coacervation based technologies, film casting, extrusion based technologies and other processes to manufacture polymer-drug microparticles possessing an extended release profile. Examples of suitable extended release technologies that can be used to incorporate the novel naltrexone forms described herein include, without limitation, the MEDISORB® technology, as described in, for example, U.S. Pat. No. 6,264,987 to Wright, U.S. Pat. Nos. 5,654,008 and/or 5,792,477, for example; the PROLEASE® technology, as described, for example in U.S. Pat. No. 6,358,443 to Herbert; the technologies described by Southern Research Institute, as described for example in U.S. Pat. Nos. 6,306,425 and 5,407,609; and "Method of Preparing Sustained Release Microparticles," U.S. Application No. 60/441,946, filed Jan. 23, 2003, and the technologies described by Alza Corp., including the ALZAMER® Depot injection technology. The contents of these patents are incorporated herein by reference in their entirety.

In another embodiment, the novel naltrexone forms described herein may be used in combination with other treatments including but not limited to psychotherapy and/or other medications. Other medications that may be combined with the long acting naltrexone of the invention include but are not limited to anticonvulsants (see U.S. Patent Application No. 60/554,658 filed on Mar. 17, 2005, incorporated herein by reference), dopamine D2 partial agonists (see U.S. Patent Application No. 60/554,785 filed on Mar. 17, 2005, incorporated herein by reference) and cannabinoid receptor antagonist. Examples of anticonvulsants useful in conjunction with the present invention include but are not limited to carbamezepine, valproic acid, lamotrigine, gabapentin, topiramate, phenobarbital, diphenylhydantoin, phenytoin, mephenytoin, ethotoin, mephobarbital, primidone, ethosuximide, methsuximide, phensuximide, trimethadione, phenacemide, acetazolamide, progabide, clonazepam, divalproex sodium, magnesium sulfate injection, metharbital, paramethadione, phenytoin sodium, clobazam, sulthiame, dilantin, zolpidem tartrate, zaleplon, indiplon, and zopiclone. Examples of dopamine D2 partial agonists useful in the present invention include but are not limited to Aripiprazole, 7-{4-[4-(2,3-dichlorophenyl)-1-piperazinyl]-butoxy}-3-,4-dihydro carbostyril or 7-{4-[4-(2,3-dichlorophenyl)-1-piperazinyl]-butoxy}-3,4-dihydro-2(1H)-quinolinone, and the partial dopamine agonist (−)3-(3-hydroxyphenyl)-N-n-propylpiperidine [(−)-3PPP, see U.S. Pat. No. 4,719,219].

In a preferred embodiment, the long acting formulation delivers therapeutically beneficial amounts of naltrexone to the patient for a period of at least one week, preferably at least about two weeks, more preferably at least about 3 or about 4 or more weeks. A four week delivery is often referred to as a monthly delivery.

In one preferred embodiment, the naltrexone is present in the extended release device or formulation in an amount of at least about 5% by weight, preferably at least about 10% by weight, more preferably at least about 30% by weight, such as about 35% by weight naltrexone of the total weight of the device, or formulation.

Alternatively, instead of incorporating naltrexone into polymeric particles, it is possible to entrap these materials in microparticles prepared, for example, by coacervation techniques or by interfacial polymerization (for example, hydroxymethylcellulose or gelatine-microcapsules and poly-(methylmethacrylate) microcapsules, respectively), in colloidal drug delivery systems (for example, liposomes, albumin, microparticles, microemulsions, nanoparticles, and nanocapsules), or in macroemulsions.

When the composition is to be used as an injectable material, including but not limited to needle-less injection, it can be formulated into a conventional injectable carrier. Suitable carriers include biocompatible and pharmaceutically acceptable solutions. The injection can be intramuscular or subcutaneous.

While the formulation may contain additional excipients, as is well known in the art, the present invention can achieve an excellent release profile with the simple formulation described herein. Such additional excipients can increase or decrease the rate of release of the agent. Ingredients which can substantially increase the rate of release include pore forming agents and excipients which facilitate polymer degradation. For example, the rate of polymer hydrolysis is increased in non-neutral pH. Therefore, an acidic or a basic excipient such as an inorganic acid or inorganic base can be added to the polymer solution, used to form the microparticles, to alter the polymer erosion rate.

A preferred embodiment of the described sustained release formulations consists essentially of the biocompatible polymer and naltrexone. By "consists essentially of" is meant the absence of ingredients which substantially increase the rate of release of the active agent from the formulation. Examples of additional excipients which would not be expected to substantially increase or decrease the rate of release of the agent include additional active agents and inert ingredients.

In yet another embodiment, the formulation consists of the biocompatible polymer and naltrexone. By "consists of" is meant the absence of components or ingredients other than those listed and residual levels of starting materials, solvents, etc. from the process.

As stated above, the formulation preferably releases naltrexone over a period of at least about one, two, three or four weeks. As such, the formulation can be administered using a dosing schedule which achieves the desired therapeutic levels for the desired period of time. For example, the formulation can be administered and, optionally, the patient monitored until levels of the drug being delivered return to baseline. Following an actual or projected return to baseline, the formulation can be administered again. Alternatively, the subsequent administration of the formulation can occur prior to achieving baseline levels in the patient. As such, the formulation can be advantageously administered weekly, with a one week release formulation, biweekly with a two week release formulation, or monthly with a four week release formulation. Vivitrex is a four week release formulation with a monthly (e.g., every four weeks) administration. The therapy can end after a single dose or can be maintained for longer periods of time. In one embodiment, the therapy can maintained for at least about 4, 8, 12, 16, 20 and 24 weeks or more. Where more than one administration is given, the second administration can be given at least about 7 days, preferably at least about 14 days, more preferably at least about 21 days, such as about 28 days, after the first administration and combinations thereof. In this context "about" preferably means within three days of the targeted date.

Particularly good results were achieved upon administering the same formulation and same dose with each administration. Thus, where a 380 mg dose was given in the first administration, good to excellent results were achieved when the second and subsequent doses were about 380 mg. Surprisingly, good to excellent results were also obtained when each dose administered contained 190 mg naltrexone, particularly in men and women who were abstinent from alcohol in the three or five days prior to commencing treatment. As such, in one embodiment of the invention, the doses and/or formulations administered in each subsequent administration were similar or the same. As stated above, the formulation is preferably a microsphere formulation and is administered by IM injection. Administration to the buttock in a volume of up to about 4 mL in an injectable diluent was performed in the trials leading up to these inventions.

The methods of the inventions achieved good to excellent results in women and, in particular, men. Good to excellent results were achieved in young individuals (defined as less than 50 years of age), particularly men. Individuals afflicted by alcohol dependency, such as a heavy drinker achieved good to excellent results. A heavy drinker is understood in the art to include women who consume four or more alcoholic beverages in a day and men who consume five or more alcoholic beverages in a day.

In yet another embodiment, the inventions include a method of increasing the days prior to occurrence of alcohol consumption in an individual in need of naltrexone comprising administering a long acting formulation comprising naltrexone in accordance with the protocols and/or dosing regimens described herein. In one embodiment, the increase in days prior to occurrence of alcohol consumption can include the consumption of a single alcoholic beverage or it can include consumption of four or five alcoholic beverages, such as the number of drinks characterizing an episode of "heavy drinking," above. In general, the greater the number of days that transpire prior to alcohol consumption indicates a more successful therapy.

EXEMPLIFICATION

Example 1

Method for Manufacturing Vivitrex® Long Acting Formulations

The invention includes a preferred method for manufacturing extended release devices, wherein the resulting device contains a mixture of the described polymorphic forms.

Polymer solution can be formed by dissolving a poly(lactide)-co-glycolide polymer, such as a 75:25 DL PLGA (poly (lactide)-co-glycolide) in a polymer solvent, such as ethyl acetate (EtAc), to form a solution. Preferred PLGA polymers are high molecular weight polymers, such as polymers possessing a molecular weight of at least about 100,000 daltons. A naltrexone solution can be formed by dissolving naltrexone base in a suitable solvent, such as benzyl alcohol (BA), to form a solution. The polymer solution and the naltrexone solution are preferably mixed together to form a drug/polymer solution that will be the "organic" or "oil" phase of the emulsion.

The "aqueous" or "continuous" phase of the emulsion (emulsifying solution) is prepared. The aqueous phase preferably contains poly(vinyl alcohol) (PVA) and polymer solvent, such as EtAc. The organic phase and the aqueous phase can be conveniently combined in a first static mixer to form an oil-in-water emulsion.

In an optional partial extraction step, the emulsion flows out of the first static mixer and into a second static mixer where the emulsion can be combined with a primary extraction solution which enters the second static mixer. The primary extraction solution (such as can be formed by an EtAc aqueous solution) can initiate solvent extraction from the microdroplets of the emulsion during the partial primary extraction step in the second static mixer.

The outflow of the first or second static mixer can flow into an extraction vessel containing primary extraction solution. The solvents (BA and EtAc) are substantially extracted from the organic phase of the emulsion in this primary solvent extraction step, resulting in nascent microparticles comprised mainly of polymer and drug. The primary solvent extraction step lasts for approximately six hours.

The microparticles can be collected, and vacuum dried, optionally with a nitrogen bleed using a customized vibratory sieve. After collection and prior to drying, the microparticles are rinsed with a 25% ethanol solution that removes the emulsifying agent (PVA), and enhances yield by aiding in the transfer of the microparticles to the cold dryer. This step is conducted, preferably at cold temperatures, until the desired level of dryness is achieved. As can be seen in the examples below, the degree of dryness (as measured, for example, by a humidity probe), impacts upon the degree of crystallinity achieved in the final product. For example, it can be advantageous to select a drying time of at least about 8, 16, 24 or 40 hours of drying. For example, it can be advantageous to select a drying time of at least about 8, 16, 24 or 40 hours where drying is 40%, 70%, 95% or 100% complete respectively. Drying is considered complete when the absolute humidity of the effluent gas reaches approximately 0 g/m$^3$.

The microparticles can then be resuspended in a second extraction solution. The second solution can contain the solvent desired to form the polymorphic form, such as ethanol. For example, a solution comprising at least about 10% by volume, preferably at least about 20% ethanol, can be used. This can be conveniently called the reslurry and secondary solvent extraction steps. The solvent, such as ethanol, can facilitate further extraction of BA and EtAc. Further, the crystallinity of the drug increases during the step. The secondary solvent extraction step is carried out in an extraction vessel for approximately two, three, four or more hours. This step can be conveniently completed at room temperature. However, other temperatures can be selected as well. In the collection/final dry step, the microparticles are collected, and vacuum dried with a nitrogen bleed using a customized vibratory sieve.

In the final harvest step, the microparticles can be transferred into a sterile container and stored, for example, in a freezer at −20° C., until filling into vials. Preferably, the stored microparticles are sieved through a 150 micron screen to remove any oversized material prior to filling into vials.

Preparation of Naltrexone Base Microparticles.

The naltrexone base microparticles were produced using a co-solvent extraction process. The theoretical batch size was 15 to 20 grams. The polymer (MEDISORB® 7525 DL polymer, MEDISORB® 8515 DL polymer and MEDISORB® 6536 DL polymer, all available from Alkermes, Inc., Blue Ash, Ohio) was dissolved in ethyl acetate to produce a 16.7% w/w polymer solution. The naltrexone base anhydrous was dissolved in benzyl alcohol to produce a 30.0% w/w solution. In various batches, the amount of drug and polymer used was varied to produce microparticles with different theoretical drug loading ranging from 30%-75%. The ambient polymer and drug solutions were mixed together until a single homogeneous solution (organic phase) was produced. The aqueous phase was at ambient conditions and contained 1% w/w polyvinyl alcohol and a saturating amount of ethyl acetate. These two solutions were pumped via positive displacement pumps at a ratio of 3:1 (aqueous:organic) through a ¼' in-line mixer to form an emulsion. The emulsion was transferred to a stirring solvent extraction solution consisting of 2.5% w/w of ethyl acetate dissolved in distilled water at 5-10° C., at a volume of 0.5 L of extraction solution per-theoretical gram of microparticles. Both the polymer and drug solvents were extracted into the extraction solution from the emulsion droplets to produce microparticles. The initial extraction process ranged from two to four hours. The microparticles were collected on a 25 μm sieve and rinsed with a cold (<5° C.) 25% w/w ethanol solution. The microparticles were dried cold overnight (approximately 17 hours) using nitrogen. The microparticles were then transferred to the reslurry solution, which consisted of a vigorously stirring 25% w/w ethanol solution at 5-10° C. After a short mixing time (five to fifteen minutes), the reslurry solution and the microparticles were transferred to a stirring 25% w/w ethanol secondary extraction solution (approximately 25° C. at a volume of 0.2 L of secondary extraction solution per theoretical gram of microparticles). The microparticles stirred for six hours enabling additional solvent removal from the microparticles to take place. The microparticles were then collected on a 25 μm sieve and rinsed with a 25% w/w ethanol solution at ambient temperature. These microparticles dried in a hood under ambient conditions overnight (approximately 17 hours), were sieved to remove agglomerated microparticles and then placed into a freezer for storage.

Preparation of Naltrexone Microspheres

A 1 kg batch of naltrexone microspheres was prepared as follows. Polymer solution was formed by dissolving 75:25 DL PLGA (poly(lactide)-co-glycolide) in ethyl acetate (EtAc) to form a solution of 16.7% polymer and 83.3% EtAc. A naltrexone solution was formed by dissolving naltrexone base in benzyl alcohol (BA) to form a solution of 30% naltrexone base anhydrous and 70% BA. The polymer solution and the naltrexone solution were mixed together to form a drug/polymer solution that was the "organic" or "oil" phase of the emulsion.

The "aqueous" or "continuous" phase of the emulsion (emulsifying solution) was prepared by dissolving poly(vinyl alcohol) (PVA) and EtAc in water-for-injection (WFI). The organic phase and the aqueous phase were combined in a first static mixer to form an oil-in-water emulsion. The droplet size of the emulsion was determined by controlling the flow rates of the two phases through the first static mixer.

In a partial primary extraction step, the emulsion flowed out of the first static mixer and into a second static mixer where the emulsion was combined with a Primary extraction solution which enters the second static mixer. The primary extraction solution (2.5% EtAc and 97.5% WFI at approximately 6° C.) initiated solvent extraction from the microdroplets of the emulsion during the partial primary extraction step in the second static mixer.

The outflow of the second static mixer (combined flow stream of the emulsion and the primary extraction solution) flowed into an extraction vessel containing primary extraction solution. The solvents (BA and EtAc) were further extracted from the organic phase of the emulsion in this primary solvent extraction step, resulting in nascent microparticles comprised mainly of polymer and drug. The primary solvent extraction step lasted for approximately six hours.

The microparticles were collected, and vacuum dried with a nitrogen bleed using a customized vibratory sieve. After collection and prior to drying, the microparticles were rinsed with a 25% ethanol solution that removes the emulsifying agent (PVA), and enhances yield by aiding in the transfer of the microparticles to the dryer.

To further reduce the solvent levels the microparticles were resuspended in a second extraction solution of 25% ethanol and 75% WFI in the reslurry and secondary solvent extraction steps. The ethanol facilitated further extraction of BA and EtAc. The secondary solvent extraction step was carried out in an extraction vessel for approximately four hours. In the collection/final dry step, the microparticles were collected, and vacuum dried with a nitrogen bleed using a second customized vibratory sieve.

In the final harvest step, the microparticles were transferred into a sterile container and stored in a freezer at −20° C. until filling into vials. Preferably, the stored microparticles were sieved through a 150 micron screen to remove any oversized material prior to filling into vials.

Example 2

Phase III Clinical Trial (also Referred to herein as "ALK21-003")

Screening and Eligibility Criteria

Participants were male or nonpregnant, nonlactating female outpatients ≧18 years old with a current diagnosis of alcohol dependence. Patients had a minimum of two episodes of heavy drinking (≧5 alcoholic drinks/day for men and ≧4 drinks/day for women) per week during the 30 days prior to screening.

Exclusion criteria included evidence of liver failure; alanine aminotransferase (ALT) or aspartate aminotransferase (AST) levels greater than three times the upper limit of normal; history of pancreatitis; major depression with suicidal ideation, psychosis, or bipolar disorder (patients with treated depression and stable pharmacotherapy for at least 8 weeks were not excluded); dependence within the past year on benzodiazepines, opiates, or cocaine; more than 7 days of inpatient treatment for substance abuse during the month prior to screening; or use of opiates, oral naltrexone, or disulfiram during the two weeks prior to screening.

Detoxification prior to randomization was performed only if indicated by investigator judgment and had to be completed seven days before initiation of study therapy. Use of benzodiazepines was prohibited during the week prior to the first dose of study medication.

Randomization Procedures

Patients were randomized to one of three treatment groups: long-acting injectable naltrexone 380 mg, long-acting injectable naltrexone 190 mg, or matching volumes of placebo (one-half of the placebo patients received an injection volume corresponding to 380 mg and the other half received an injection volume corresponding to 190 mg). The study used a dynamic randomization procedure to balance allocation on gender, patient-specified goal of total abstinence, self-reported abstinence for the 7-day period prior to first injection, and study site.

Study Procedures and Outcome Definitions

Patients received an injection of study medication at 4-week intervals over 24 weeks, alternating between the left and right gluteus maximus. Injections were prepared and administered by individuals who were not involved in any of the safety or efficacy assessments, and treatment assignment was blinded to all study personnel.

All patients received standardized supportive therapy (12 sessions) using the BRENDA model (Volpicelli J R, Pettinati H M, McLellan A T, O'Brien C P. *Combining medication and psychosocial treatments for addictions: the BRENDA approach*. New York: The Guilford Press; 2001), a six-stage low-intensity intervention designed to facilitate direct feedback with respect to addiction-related consequences. During this trial, BRENDA sessions were administered by study site personnel including psychologists, nurses, therapists, counselors, and physicians.

The number of standard drinks consumed per day was recorded using the Timeline Follow Back (TLFB) method (Sobell L C, Sobell M B. *Timeline Followback: a technique for assessing self-reported ethanol consumption*, In: Allen J, Litten R Z, eds. Measuring alcohol consumption: psychosocial and biological methods. Totowa, N.J.: Humana Press, 1992:41-72). Breath alcohol levels of ≦0.02 gm/dL were required before self-report data were collected. Patients who discontinued study drug treatment prematurely were allowed to remain in the study, continue to follow the established visit and procedure schedule, and receive BRENDA treatment.

Study Formulation: Naltrexone long-acting injection (Vivitrex®) consists of microspheres (approximately 100 μM) composed of naltrexone and polylactide-co-glycolide polymeric matrix (Medisorb®), a common biodegradable medical polymer with an extensive history of human use in absorbable sutures and extended-release pharmaceuticals. Following injection, naltrexone on the surface of the microspheres is released, yielding peak concentrations within three days. Thereafter, by a combination of diffusion and erosion, naltrexone is further released for greater than 30 days.

Definition of Outcomes. The primary efficacy endpoint was the event rate of heavy drinking over the 24 weeks of treatment. The definition of heavy drinking (≧5 drinks per day for men and ≧4 drinks per day for women) is consistent with that used in previous trials of oral naltrexone. Secondary endpoints included the event rate of "risky" drinking (>2 drinks per day for men and >1 drink per day for women) specified by the National Institute on Alcohol Abuse and Alcoholism (NIAAA) (U.S. Department of Agriculture/U.S. Department of Health and Human Services. Home and Garden Bulletin no. 232. *Nutrition and your health: dietary guidelines for Americans*. 3rd ed. Washington, D.C.: Supt. of Docs., U.S. Government. Printing Office, 1990), and the event rate of any drinking days. Secondary endpoints included median relapse to heavy drinking, NIAAA-derived "safe drinking" any drinking, and number of alcoholic drinks per day. Exploratory endpoints included serum gamma-glutamyl transferase (GGT) changes over time, and time to patient discontinuation. Adverse events were coded using the MedDRA dictionary of preferred terms.

Statistical Methods

The primary analysis for the primary and secondary endpoints was performed on an intention-to-treat population (i.e., all randomized patients who received at least one dose of study medication). The primary objective was to determine whether treatment with long-acting naltrexone (at either 190 mg or 380 mg) decreased the event rate of heavy drinking relative to treatment with placebo injection. Statistical methods to analyze multiple drinking episodes in alcoholism treatment clinical trials have been described by Wang et al., Short of complete abstinence: an analysis exploration of multiple drinking episodes in alcoholism treatment trials. Alcohol Clin Exp Res. 2002; 26:1803-9. The primary analysis for the primary endpoint was performed using a stratified recurrent event Andersen-Gill like model with robust variance estimation (Lin D Y, Wei L J, Yang I, and Ying Z. *Semiparametric regression for the mean and rate functions of recurrent events*. J Royal Stat Soc (B) 2000; 62: 711-30; SAS/STAT user's guide. Version 8. Cary, N.C.: SAS Institute, 1999:2596). The parameters estimated in the model were those representing the treatment effect of 190 mg relative to placebo and 380 mg relative to placebo. The analysis was performed on all heavy drinking events captured during the treatment period reflecting the days between first treatment and 30 days following the last dose of study medication. Analyses of the primary endpoint were performed by gender and for each of the other predefined stratification variables. Retention rates were evaluated by generating Kaplan-Meier curves for the time to study discontinuation. A log rank test was used to examine treatment group differences.

RESULTS 624 patients were randomly assigned and received treatment, constituting the intention-to-treat population for analyses, according to the flow chart below:

Patients were predominantly male (68%) and Caucasian (84%), with a mean age of 45 years (range 19-74). Baseline drinking averaged 20 (SD=8) heavy drinking days over the 30 days prior to study entry. Overall, 8.8% of patients were abstinent during the 7-day lead-in period and 43% of the patients had a goal of total abstinence. Pretreatment characteristics of the patients in the three treatment groups were similar (Table 1).

Overall, 401 patients (64%) received all 6 injections, and 378 patients (61%) completed the trial. Time to discontinuation was similar among groups. The median number of therapy sessions completed was 11 out of a maximum of 12 and 42.8% of patients attended all therapy sessions. The number of therapy sessions and the percentage of patients attending all sessions were similar among treatment groups.

TABLE 1

Base-line characteristics of the patients (ITT population)

| Demographic and other variables | Long-acting naltrexone 380 mg (N = 205) | | | Long-acting naltrexone 190 mg (N = 210) | | | Placebo (N = 209) | | |
|---|---|---|---|---|---|---|---|---|---|
| | Overall | Males | Females | Overall | Males | Females | Overall | Males | Females |
| Age (yr) | 45.0 ± 10.1 | 45.4 ± 10.9 | 44.2 ± 8.3 | 44.6 ± 10.8 | 44.6 ± 11.5 | 44.6 ± 9.3 | 44.7 ± 10.8 | 44.7 ± 11.2 | 44.6 ± 10.0 |
| Gender | | | 67 | | | 68 | | 143 | 66 |
| No. of patients (%) | | 138 (67.3) | (32.7) | | 142 (67.6) | (32.4) | | (68.4) | (31.6) |
| Race or ethic group (%) | | | | | | | | | |
| White* | 83.9 | 81.9 | 88.1 | 80.5 | 78.9 | 83.8 | 86.1 | 83.2 | 92.4 |
| Weight (kg)* | 84.2 ± 20.7 | 90.5 ± 19.2 | 71.1 ± 17.5 | 82.7 ± 19.8 | 88.7 ± 19.2 | 70.5 15.3 | 81.6 ± 17.0 | 86.1 ± 15.5 | 71.9 ± 16.2 |
| Employment status | | | | | | | | | |
| (% employed ≧ 20 hr/week) | 70.2 | 71.0 | 68.7 | 71.0 | 73.9 | 64.7 | 72.2 | 72.0 | 72.7 |
| Current (%) smoker* | 48.5 | 53.3 | 38.8 | 50.7 | 53.9 | 44.1 | 42.3 | 45.8 | 34.8 |
| Current antidepressant use (%)* | 30.2 | 21.7 | 47.8 | 26.3 | 21.3 | 36.8 | 29.2 | 24.5 | 39.4 |
| Liver enzymes | | | | | | | | | |
| AST*† | 30.0 ± 13.1 | 32.5 ± 14.3 | 24.7 ± 8.0 | 32.7 ± 17.4 | 35.7 ± 18.6 | 26.4 ± 12.5 | 31.9 ± 18.1 | 33.8 ± 18.5 | 27.7 ± 16.5 |
| ALT*† | 31.9 ± 19.2 | 37.3 ± 20.5 | 20.8 ± 8.6 | 32.9 ± 20.6 | 38.2 ± 22.1 | 21.8 ± 10.9 | 34.0 ± 21.8 | 38.1 ± 22.4 | 25.0 ± 17.6 |
| GGT* | 58.6 ± 60.8 | 67.7 ± 63.8 | 39.8 ± 49.7 | 73.5 ± 86.4 | 86.6 ± 90.5 | 46.1 ± 70.3 | 75.6 ± 113.9 | 87.2 ± 127.3 | 50.5 ± 72.0 |
| Goal of abstinence (%) | 43.9 | 47.1 | 37.3 | 42.9 | 41.5 | 45.6 | 43.1 | 45.5 | 37.9 |
| Heavy drinking days in 30 prior to first dose (%) | 64.0 ± 25.9 | 63.5 ± 26.5 | 65.0 ± 24.8 | 65.6 ± 26.4 | 64.6 ± 25.4 | 67.7 ± 28.4 | 65.2 ± 24.8 | 65.2 ± 24.5 | 65.2 ± 25.5 |
| Abstinence for 7 days prior to first dose (%) | 8.3 | 9.4 | 6.0 | 8.1 | 7.0 | 10.3 | 9.1 | 10.5 | 6.1 |
| Self-help group attendance (%)* | 11.7 | 13.0 | 9.0 | 10.5 | 12.0 | 7.4 | 11.0 | 13.3 | 6.1 |

Plus-minus values are mean ± standard deviation.
AST = aspartate aminotransferase;
ALT = alanine aminotransferase;
GGT = γ-Glutamyltransferase
*P > 0.05 (significant difference between men and women in the overall study population [N = 624]).
†The normal values for AST and ALT are gender and age specific:
ALT: Women 18-69 yr: 6-34 U/L, >69 yr: 6-32 U/L; Men 18-69 yr: 6-43 U/L, >69 yr: 6-35 U/L
AST: Women ≧ 18: 9-34 U/L; Men ≧ 18: 11-36 U/L Adverse events occurring in ≧10% of the patients during treatment with long-acting injectable naltrexone are listed in Table 2.

TABLE 2

Adverse events during treatment occurring in 10% or more of patients

| Adverse Event, no. (%) | Long-acting naltrexone 380 mg (N = 205) | Long-acting naltrexone 190 mg (N = 210) | Placebo (N = 209) |
|---|---|---|---|
| Nausea | 70 (34%)*† | 53 (25%)* | 23 (11%) |
| Headache | 46 (22%) | 33 (16%) | 34 (16%) |
| Fatigue | 42 (21%)* | 35 (17%) | 23 (11%) |
| Insomnia | 28 (14%) | 27 (13%) | 25 (12%) |
| Vomiting | 28 (14%)* | 22 (11%) | 12 (6%) |
| Decreased appetite | 26 (13%)*† | 12 (6%)* | 3 (1%) |
| Diarrhea | 26 (13%) | 23 (11%) | 18 (9%) |
| Dizziness | 26 (13%)* | 23 (11%)* | 8 (4%) |
| Nasopharyngitis | 25 (12%) | 32 (15%) | 24 (12%) |
| Injection site pain | 23 (11%)* | 18 (9%) | 12 (6%) |
| Upper respiratory tract infection | 21 (10%) | 15 (7%) | 18 (9%) |

*$P < 0.05$ vs placebo.
†$P < 0.05$ vs Vivitrex 190 mg.
Note:
Percentages are based on the number of patients in the ITT population (dosed at least once). Fischer's exact test used for association of treatment by adverse event; pair-wise comparisons with 2 × 2 tables.

Other adverse events, which occurred in less than 10% of subjects but more frequently in the long-acting naltrexone subjects ($P<0.05$) included the following: abdominal pain, injection site induration, injection site pruritus, decreased libido, and arthralgia.

The most common adverse events were nausea, headache, and fatigue. Nausea was mild or moderate in approximately 95% of cases, the large majority of which occurred during the first month of treatment, with a median duration of 1 day. Nausea and decreased appetite occurred more frequently in patients treated with the long-acting naltrexone 380 mg.

Study discontinuation secondary to adverse events occurred in 14.1% (naltrexone 380 mg), 6.7% (naltrexone 190 mg) and 6.7% (placebo) of patients (P=0.013, 380 mg vs. 190 mg and placebo). The percentage of patients who experienced serious adverse events (SAEs) during treatment was similar among the treatment groups: 6.3% (n=13) for naltrexone 380 mg, 5.2% (n=11) for naltrexone 190 mg, and 7.2% (n=15) for placebo, with the most common SAE being hospitalization for alcohol detoxification. Two SAEs (eosinophilic pneumonia and interstitial pneumonia) were judged to be possibly related to study medication. Both events occurred in patients treated with naltrexone 380 mg and resolved with treatment. The most common injection site reaction was tenderness, occurring after 15.9% of 380 mg doses and 13.6% of 190 mg doses, and after 17.6% of high-volume placebo injections and 9.2% of low-volume placebo injections. Seven patients discontinued injections due to site reactions: 4 naltrexone 380 mg patients, 2 naltrexone 190 mg patients, and 1 high-volume placebo patient.

Mean AST and ALT levels, did not change significantly over the course of treatment or with medication. Furthermore, long-acting naltrexone was not associated with an increased rate of AST or ALT elevations above three times the upper limit of normal.

Analyses of primary and secondary efficacy variables measured during the 6-month treatment period are listed in Table 3.

TABLE 3

Analyses of Primary and Secondary Efficacy Outcomes

| | | | Naltrexone 190 mg vs Placebo | | Naltrexone 380 mg vs Placebo | |
|---|---|---|---|---|---|---|
| | Stratification Variable | Population | Hazard Ratio (95% CI) | P value | Hazard Ratio (95% CI) | P value |
| Primary Outcome | | | | | | |
| Heavy Drinking | Overall Sample | Overall | 0.83 (0.68, 1.02) | 0.076 | 0.75 (0.60, 0.94) | 0.025 |
| | Gender | Male | 0.75 (0.58, 0.95) | 0.020 | 0.52 (0.38, 0.69) | <0.0001 |
| | | Female | 1.05 (0.73, 1.51) | 0.79 | 1.29 (0.91, 1.83) | 0.31 |
| | Goal of Total Abstinence | Yes | 0.88 (0.61, 1.28) | 0.50 | 0.72 (0.48, 1.08) | 0.11 |
| | | No | 0.91 (0.70, 1.18) | 0.48 | 0.79 (0.59, 1.05) | 0.01 |
| | Lead-in Drinking | Yes | 0.93 (0.75, 1.15) | 0.48 | 0.79 (0.62, 1.00) | 0.05 |
| | | No | 0.05 (0.02, 0.15) | <0.0001 | 0.20 (0.07, 0.62) | 0.005 |
| Secondary Outcomes | | | | | | |
| "Risky" drinking | Overall Sample | Overall | 0.93 (0.80, 1.08) | 0.32 | 0.92 (0.80, 1.07) | 0.30 |
| | Gender | Male | 0.86 (0.70, 1.04) | 0.11 | 0.72 (0.58, 0.89) | 0.002 |
| | | Female | 1.04 (0.83, 1.31) | 0.73 | 1.20 (0.97, 1.49) | 0.094 |
| Nonabstinent days | Overall Sample | Overall | 0.93 (0.82, 1.06) | 0.30 | 1.00 (0.88, 1.14) | 0.98 |

TABLE 3-continued

Analyses of Primary and Secondary Efficacy Outcomes

| | | Naltrexone 190 mg vs Placebo | | Naltrexone 380 mg vs Placebo | |
|---|---|---|---|---|---|
| Stratification Variable | Population | Hazard Ratio (95% CI) | P value | Hazard Ratio (95% CI) | P value |
| Gender | Male | 0.93 (0.78, 1.09) | 0.37 | 0.87 (0.73, 1.04) | 0.12 |
| | Female | 0.95 (0.77, 1.16) | 0.61 | 1.19 (0.98, 1.44) | 0.081 |

*National Institute on Alcohol Abuse and Alcoholism-specified level of "risky drinking" is ≧ 2 drinks per day for men and one drink for woman.
Note:
For the primary endpoint (heavy drinking), the Hochberg method was used to adjust multiple comparisons. As specified a priori, the secondary outcomes (drinking above the NIAAA-specified level of "risky" drinking and nonabstinent days) are included for informational purposes, and no adjustments were made.

Figure 1A:
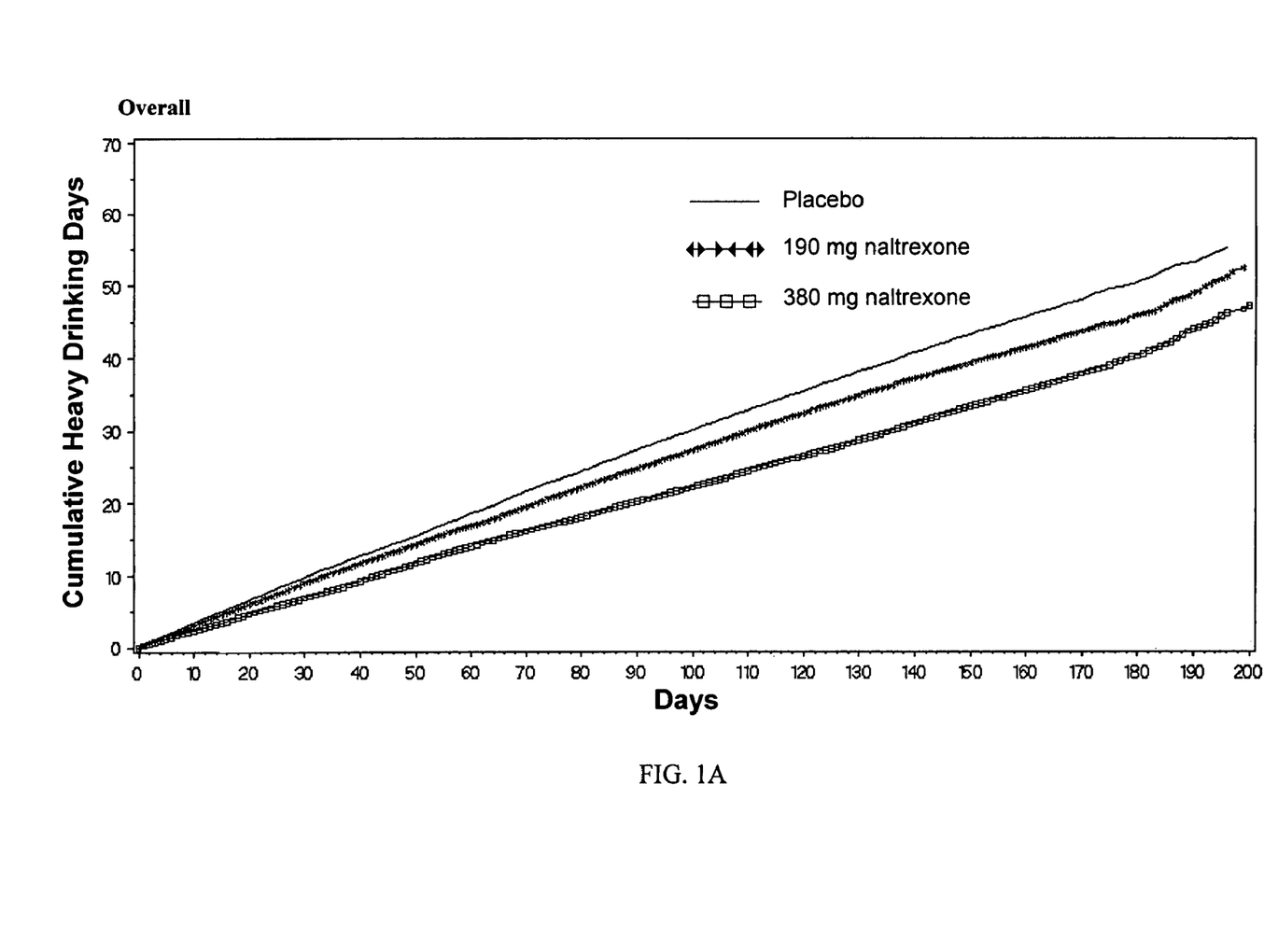
FIGS. 1A-1C shows the cumulative mean event rate of heavy drinking during the study by treatment group and gender. As an example, at day 100, the mean number of cumulative heavy drinking days for the overall study population was 22.3 for the long-acting naltrexone 380 mg patients, 27.3 for long-acting naltrexone 190 mg patients, and 30.0 for placebo patients.
Figure 1B:
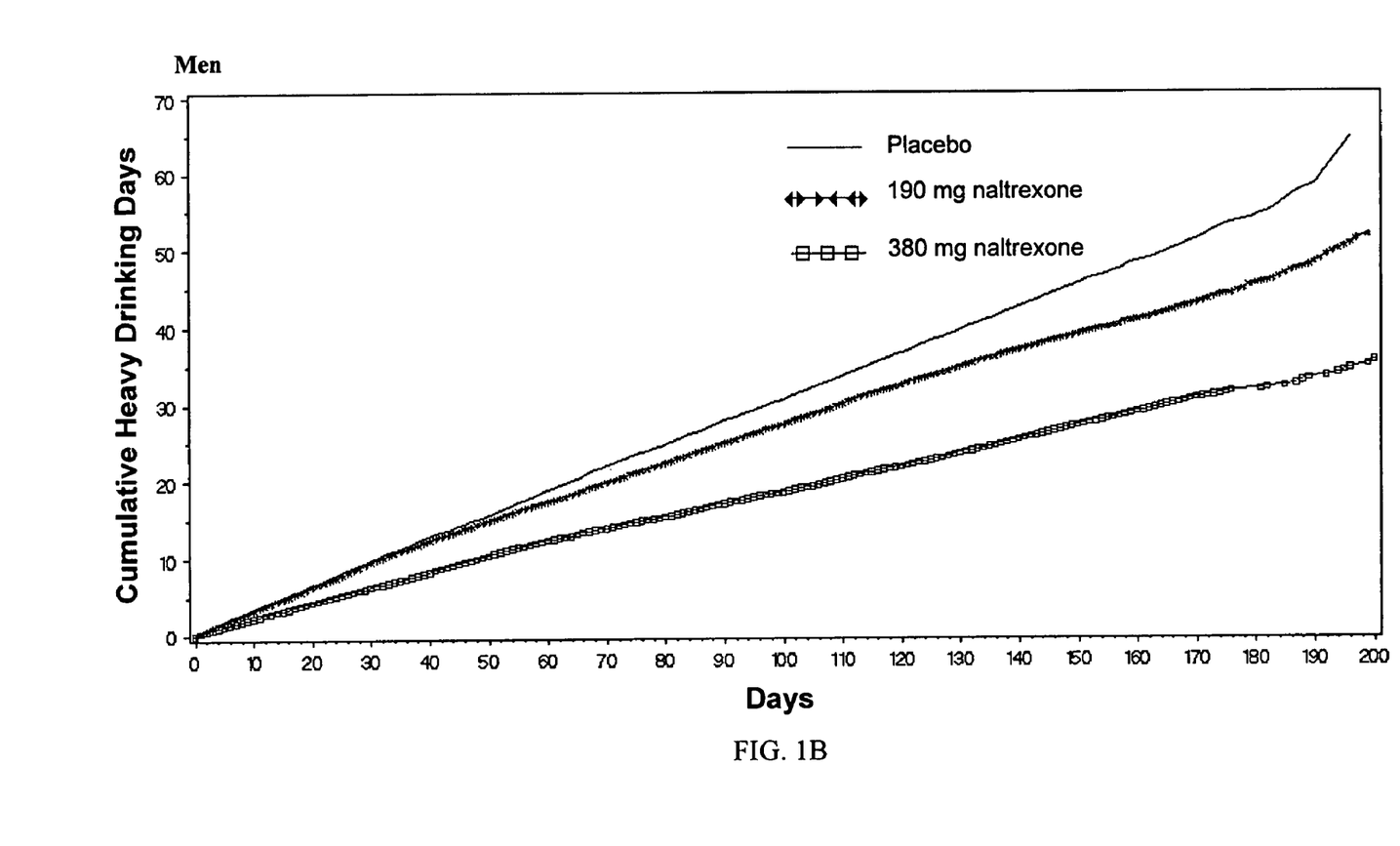
Figure 1C:
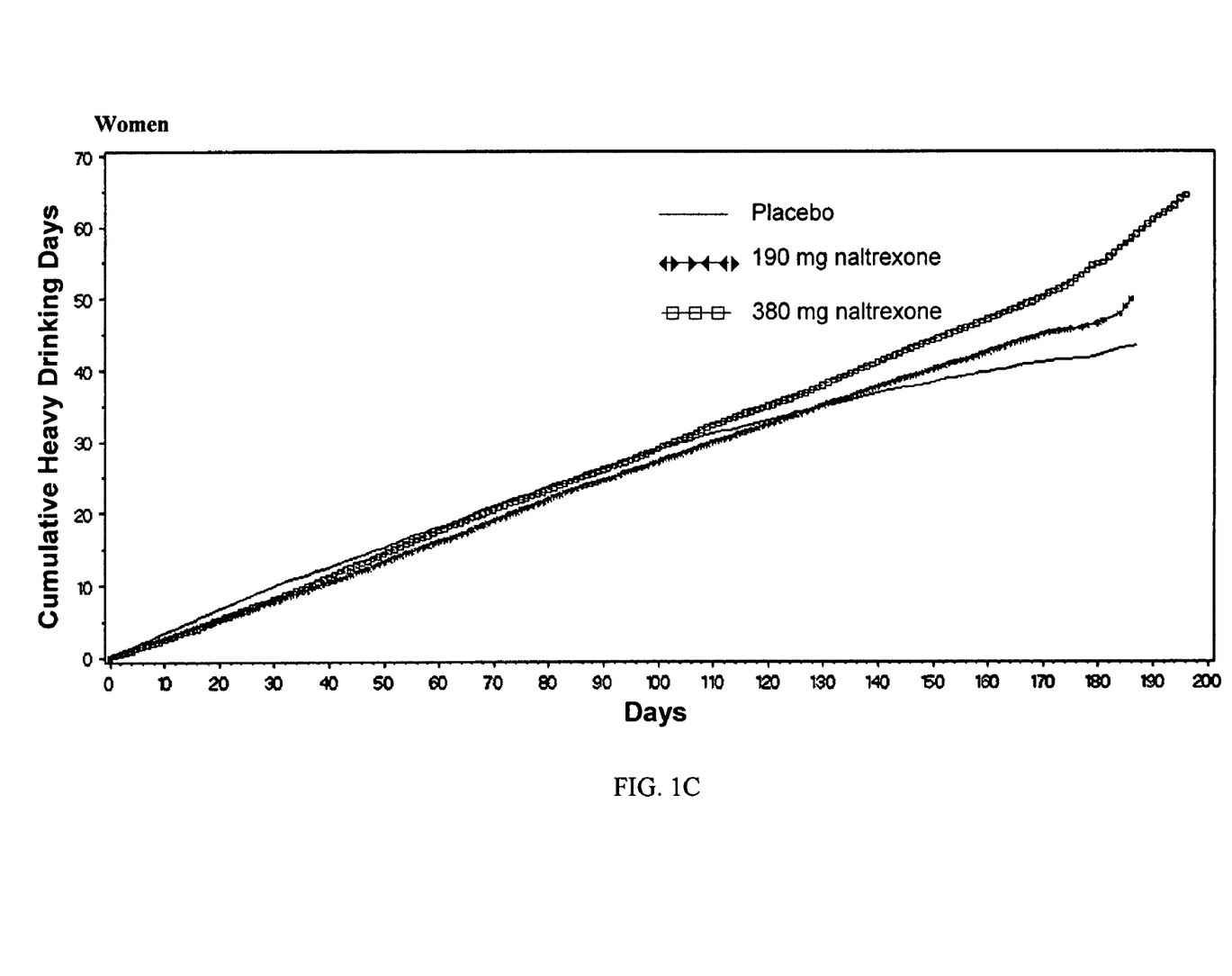

Overall, patients treated with long-acting naltrexone 380 mg experienced approximately a 25% greater reduction in the rate of heavy drinking than placebo-treated patients (P<0.025) (FIG. 1). The reduction in heavy drinking was greatest in men treated with naltrexone 380 mg (n=138), who showed a 48% greater reduction in the rate of heavy drinking than placebo-treated patients (n=143) (P<0.001). In contrast, no significant differences were observed between women treated with naltrexone 380 mg (n=67) and those receiving placebo (n=66).

Overall, patients treated with naltrexone 190 mg reported a 17% greater reduction in the rate of heavy drinking than placebo-treated patients (P=0.076). The effect of naltrexone 190 mg was more pronounced for men (n=142), who experienced approximately a 25% greater reduction in the rate of heavy drinking than placebo (n=143) (P=0.020). As with 380 mg, women treated with naltrexone 190 mg (n=68) showed no significant difference from placebo (n=66).

The other predefined stratification variables—goal of total abstinence and lead-in drinking—also influenced heavy drinking in the overall sample. Patients who had a goal of total abstinence (n=270) experienced a 39% greater reduction in heavy drinking relative to patients who did not (n=354), and those who were abstinent during the week prior to treatment (n=53) had a 76% greater reduction in heavy drinking compared to those who drank during that week (n=571). With respect to medication effects, the relative reduction in heavy drinking associated with the 380 mg and the 190 mg dose compared to placebo was similar whether or not participants had a goal of total abstinence as shown in Table 3. In contrast, the effect of treatment with the 380 mg dose and the 190 mg dose relative to the placebo dose was most pronounced in the subgroup that was abstinent at randomization compared to the subgroup that was not abstinent (Table 3). However, this latter finding must be interpreted cautiously in light of the small sample size for the group with no lead-in drinking (n=53).

Consistent with observed reductions in heavy drinking, there was a 15% reduction in GGT during the study compared to pretreatment for the overall sample. Men treated with long-acting naltrexone had a 20% and 24% reduction in GGT for the 380 mg and 190 mg groups, respectively, compared to 12% for placebo. No difference from placebo was seen in the women.

The rate of NIAAA "risky" drinking was not significantly lower with long-acting naltrexone in the overall sample but was significantly reduced (by 28%) in men who received injections of naltrexone 380 mg (see Table 3). No effect was shown on the rate of drinking days for the overall population or separately for men or women (Table 3).

Figure 2:
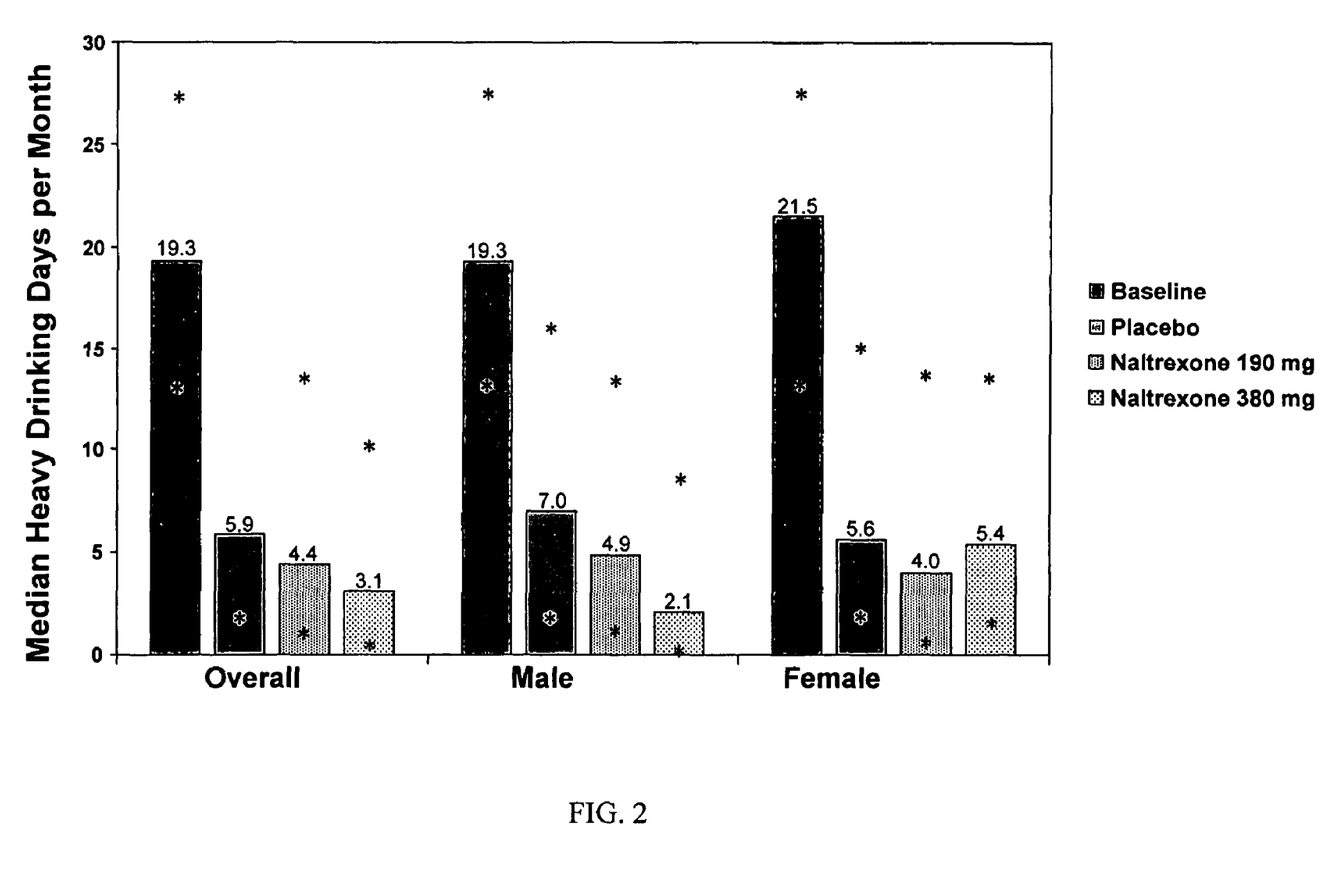
FIG. 2 shows median heavy drinking days per month for each treatment group, overall and by gender. Asterisks represent interquartile range (25%, 75%).

During the treatment period, patients in all three groups demonstrated substantial reductions from their baseline levels of heavy drinking days. FIG. 2 shows the change from baseline in the median number of heavy drinking days per month, by treatment group and gender.

This study enrolled a population of predominantly actively drinking patients, only 8.3% of whom were abstinent for the 7-day period prior to treatment. The number of patients who maintained complete abstinence during the trial was 7% in the naltrexone 380 mg group, 6% in the 190 mg naltrexone group, and 5% in the placebo group. The proportion of patients who experienced at least one heavy drinking day was 83% for naltrexone 380 mg, 86% for naltrexone 190 mg, and 89% for placebo. There were no significant group differences on either of these measures.

The median number of days to first heavy drinking event overall was 3 for the placebo group, 4 for the 190 mg group and 6 for the 380 mg group (Table 4). The difference between the 380 mg group and placebo was statistically significant (log rank test, P=0.0111). Evidence of more pronounced treatment effects were seen with Vivitrex suspension 190 mg and 380 mg in the subgroups of subjects who were abstinent 4 days prior to first study dose and those with no lead in drinking compared with the population overall.

To more comprehensively assess the effects of Vivitrex suspension, analyses of the secondary endpoints were also performed using the predefined subpopulation of subjects who had no lead-in drinking (abstinent during the 7 days immediately prior to randomization) and a larger subpopulation of subjects who were abstinent during the 4 days immediately prior to randomization. These subjects are most analogous to subjects historically studied with oral naltrexone which generally required minimum 3 to 5 days of abstinence prior to randomization.

TABLE 4

Median Number of Days to Relapse to First Heavy Drinking Event

| SUBGROUP | PLACEBO | 190 MG | 380 MG |
|---|---|---|---|
| ITT Population | 3 | 4 | 6* |
| Abstinent During the 4 Days Prior to Randomization | 20 | 47 | 181† |
| No Lead-in Drinking (Abstinent During the 7 Days Prior to Randomization) | 29 | >170 | 181 |

*P = 0.011, 380 mg compared with placebo
†P = 0.042, 380 mg compared with placebo

DISCUSSION

The main findings of this study were that a long-acting, injectable formulation of naltrexone, in conjunction with psychosocial treatment, significantly reduced heavy drinking in a large, geographically varied sample of treatment-seeking patients with alcohol dependence. These findings were most evident in men, with the median male subject reporting 7% heavy drinking days at the 380 mg dose compared to 23% heavy drinking days with placebo. In addition, the efficacy of the 380 mg dose was evident within the first month after the initial injection, and was robust over the 180-day treatment period, irrespective of whether there was drinking in the week before the first injection or the patient's goal at treatment entry was total abstinence. Importantly, naltrexone injections were well tolerated, few serious adverse events were reported, and there was no evidence of hepatotoxicity.

The primary outcome measure in this study—heavy drinking—is the sine qua non of alcoholism, and is both clinically meaningful and of public health importance. Of the various measures of drinking behavior, heavy drinking shows the highest correlation with negative life consequences such as impaired driving, interpersonal problems, and injuries. Substantial reductions in heavy drinking, as seen among men treated with naltrexone 380 mg, can be expected to lead to improvements in various areas of health and in the quality of life.

Over the last decade, studies of oral naltrexone have yielded modest evidence of efficacy, which may explain, in part, why naltrexone has not been commonly used in the clinical management of alcoholism. The effectiveness of oral naltrexone may be undermined by patients stopping or skipping their doses. Therefore, the encouraging results from the present study using the long-acting 380 mg naltrexone formulation are likely to increase confidence among clinicians that a pharmacological option exists to treat alcohol dependence. Furthermore, this study enrolled subjects without an abstinence requirement. This is in contrast to the majority of prior studies which limited enrollment to subjects who had achieved short term abstinence.

This study is the first to examine prospectively the effect of gender on response to naltrexone. Results of the multiple-event rate analysis showed a clear advantage for naltrexone over placebo among men but not women. Nonetheless, the women in this trial reduced their heavy drinking substantially, irrespective of whether they received active medication. One possible explanation for the gender difference is that women may have received a greater therapeutic benefit from the psychosocial intervention. Further evaluation of factors that may explain the differential response in women is needed utilizing a sample that is large enough to yield adequate statistical power.

In addition, the pharmacokinetic profile of long-acting injectable naltrexone differs substantially from that of the oral formulation. Peak naltrexone levels and the generation of 6-β-naltrexol via first-pass metabolism may contribute to reduced tolerability of oral naltrexone. A long-acting injectable naltrexone formulation may mitigate these effects by both eliminating daily naltrexone peaks and decreasing the ratio of 6-β-naltrexol to the parent compound compared with oral treatment (Kranzler H R, Modesto-Lowe V, Nuwayser E S. *Sustained-release naltrexone for alcoholism treatment: a preliminary study*. Alcohol Clin Exp Res 1998; 22:1074-9; Verebey K, Volavka J, Mule S J, Resnick R B: *Naltrexone: disposition, metabolism, and effects after acute and chronic dosing*. Clin Pharmacol Ther 1976; 20:315-28).

In summary, the results from this trial, one of the largest studies ever conducted to evaluate a medication for treatment of alcohol dependence, provide evidence that long-acting injectable naltrexone is a safe and effective medication for this indication, particularly among men. This formulation should be a valuable addition to the treatments that are currently available for use in alcoholism rehabilitation.

Example 3

Comparison of Efficacy with Long-Acting Naltrexone Injectable Versus Oral Naltrexone A comparison of efficacy between the long-acting naltrexone formulations of the invention and oral naltrexone was performed. As a direct head-to-head comparison of efficacy has not been studied, a definitive comparison of efficacy between Vivitrex and oral naltrexone cannot be made. Nevertheless, 3 recent meta-analyses of the efficacy with oral naltrexone (Srisurapanont M, Jarusuraisin N. *Opioid antagonists for alcohol dependence*. The Cochrane Database of Systematic Reviews 2005, Issue 1. Art. No.: CD001867.pub2. DOI: 10.1002/14651858.CD001867.pub2. This version first published online: 24 Jan. 2005 in Issue 1, 2005. Date of most recent substantive amendment: 5 Nov. 2004; Bouza C, Magro A, Munoz A, Amate J M. *Efficacy and safety of naltrexone and acamprosate in the treatment of alcohol dependence: a systematic review*. Addiction. 2004 July; 99(7):811-828; Hopkins, John Sloan, Master Paper Presentation entitled: *Meta Analysis of Clincal Trials of Naltrexone and Acamprosate for the Treatment of Alcoholism—What does the evidence tell us?* UNC-CH Department of Epidemiology, presented at the Research Society for Alcoholism Annual Scientific Meeting, Mar. 25, 2002) provide useful historical standards for a semi-quantitative comparison.

The most commonly used endpoint for oral naltrexone has been the dichotomous outcome, relapse to heavy drinking (yes/no). The studies of oral naltrexone have generally evaluated subjects who have been abstinent for 3-5 days over a 12-week treatment period. The corresponding endpoint and population; the rate of relapse to heavy drinking at 12 weeks in subpopulation of subjects in ALK21-003 Phase III clinical study who were abstinent during the 4 days immediately prior to randomization was therefore selected to compare to the results of oral studies.

In Hopkins (supra), a quantitative meta-analysis was undertaken, in which the oral naltrexone versus placebo risk differences for the dichotomous outcome—relapse to heavy drinking (yes or no)—were obtained from applicable studies. Nine studies were included. In the fixed effects model, the estimate of the combined risk difference was 0.13 (13%) with 95% confidence interval (0.08, 0.17). This result suggested a treatment effect favoring oral naltrexone.

In ALK21-003, there were 56 subjects dosed (28 placebo, 28 Vivitrex 380 mg) who were abstinent for 4 days prior to receiving study drug. At 12 weeks, the relapse rate was $11/28$ (0.39) in the Vivitrex 380 mg treatment group compared with $20/28$ (0.71) in the placebo group. The risk difference (95% CI) in this subset of subjects is 0.32 (32%) with a 95% confidence interval (0.08, 0.58). The result with Vivitrex suspension thus compares favorably with the overall risk difference determined, by Hopkins in a similar subject population.

In the Cochrane analysis (supra), the outcome, relapse to heavy drinking, was also used as the endpoint in the meta-analysis. Instead of the risk difference, results are described in terms of the relative risk (RR). At 12 weeks, oral naltrexone significantly decreased the relapse rate by 36% relative to placebo (RR [95% CI]=0.64[0.51, 0.82]). Using the relapse rates described above for the subjects who were abstinent during the 4 days prior to randomization in the ALK 21-003 study, Vivitrex suspension 380 mg significantly decreased the relapse rate by 45% relative to placebo (RR [95% CI]=0.55 [0.33, 0.92]).

Bouza, et al, supra, report the reduction of the relapse rate of their meta analysis of short term studies (≦12 weeks) in terms of the odds ratio [OR, (95% CI):0.62, (0.52,0.75)]. This analysis indicated that the odds of relapsing to heavy drinking in subjects treated with oral naltrexone decreased 38% relative to placebo. Using the relapse rates previously described above for the applicable subjects in the ALK21-003 study the reduction of the relapse rate odds ratio is [OR, (95% CI):0.26, (0.08,0.79)]. The odds of relapsing to heavy drinking of subjects treated with Vivitrex suspension 380 mg decreased 74% relative to placebo.

TABLE 5

Comparison of Results in ALK21-003 and 3 Published Meta-Analyses of Oral Naltrexone

|  | ALK21-003* 380 mg vs placebo | Hopkins et al oral vs placebo | The Cochrane Review oral vs placebo | Bouza, et al oral vs placebo |
|---|---|---|---|---|
| Risk difference (95% CI) | 0.32 (0.08, 0.58) (32% reduction) | 0.13 (0.08, 0.17) (13% reduction) | — | — |
| Relative risk (95% CI) | 0.55 (0.33, 0.92) (45% reduction) | — | 0.64 (0.51, 0.82) (36% reduction) | — |
| Odds ratio (95% CI) | 0.26 (0.08, 0.79) (74% reduction) | — | — | 0.62 (0.52, 0.75) (38% reduction) |

*Based on results of the ALK21-003 study as described in the ALK21-003 final CSR.

Based on semi-quantitative comparisons to these 3 meta-analyses, the efficacy of Vivitrex suspension compares favorably with oral naltrexone.

Example 4

Effect of Long-Acting Injectable Naltrexone on Quality of Life

Objective: Assess the effect of long-acting injectable naltrexone (LA-NTX) on health-related quality of life (QoL) in patients with alcohol dependence.

Method: A 24-week, multicenter, double-blind, placebo-controlled study evaluated the safety and efficacy of LA-NTX, a polylactide microsphere intramuscular formulation of naltrexone given monthly. DSM-IV alcohol-dependent patients (N=624) were randomized to 6 monthly injections of LA-NTX 380 mg, LA-NTX 190 mg, or placebo in combination with psychosocial support (BRENDA, see Volpicelli, infra). QoL was assessed using SF-36v2.0 (see Ware, infra).

Results: Baseline SF-36 Mental Component Scores (MCS) were 38.7, 40.3, and 40.6 for the 380 mg, 190 mg, and placebo groups, respectively (significantly lower than US population norms. Following treatment, MCS increased by 7.9, 6.2, 6.0, in the 380 mg, 190 mg, and placebo groups. The change from baseline was significant for all treatment groups (P<0.001) and was greater with 380 mg vs. placebo (P<0.05). Improvements correlated positively with reduction in alcohol consumption. Physical Component Scores (normal at baseline for all groups) did not change with treatment.

Conclusion: A large sample of alcohol-dependent patients demonstrated deficits in mental health-related QoL, which improved significantly with treatment for alcohol dependence. LA-NTX plus psychosocial therapy showed improvements in QoL that were greater than treatment with psychosocial therapy alone.

Example 5

Durability of Effect of Long-Acting Injectable Naltrexone

Objective: To assess the durability of effect and tolerability of long-acting injectable naltrexone (LA-NTX) in a 1-year extension study in patients with alcohol dependence.

Methods: A 24-week, multicenter, double-blind, placebo-controlled study evaluated the safety and efficacy of LA-NTX, a polylactide microsphere intramuscular formulation of naltrexone. DSM-IV alcohol-dependent patients (N=624) were randomized to 6 monthly injections of LA-NTX 380 mg, LAN-TX 190 mg, or placebo in combination with psychosocial support (BRENDA, Volpicelli et al., *Combining medication and psychosocial treatments for additions: the BRENDA approach*. New York: The Guilford Press; 2001). 61% of patients completed the study, of whom 85% (N=332) enrolled in a 1-year open-label extension. Alcohol intake was recorded in the base and extension studies by the Timeline Followback method (Ware et al., *How to score version 2 of the SF-36®*, Lincoln R.I.: QualityMetric Incorprated; 2000).

Results: Patients randomized to 380 mg in the base study continued to receive 380 mg in the extension study (N=115). Mean percent heavy drinking days was similar in the base study (22.7%) and the extension (19.6%) study (P=NS). Patients treated with BRENDA and placebo injections who were switched to 380 mg in the extension (N=60) showed significant reduction in percent heavy drinking days (P<0.01). Once-monthly injections of LA-NTX were well tolerated.

Conclusions: Reduction in alcohol intake observed with LA-NTX and BRENDA during a 24-week double-blind study were durable and maintained during a 1-year open-label extension study.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating an individual in need of naltrexone comprising the step of parenterally administering a long acting formulation comprising about 310 mg to about 480 mg of naltrexone and a biocompatible polymer to the individual wherein the serum AUC of naltrexone is about three times greater than that achieved by 50 mg/day oral administration and wherein the biocompatible polymer is a polylactide-co-glycolide polymer.

2. The method of claim 1 comprising administering the long acting formulation comprising naltrexone every four weeks for a period of about 24 weeks or more wherein the individual has not used oral naltrexone within five or more days before said administration.

3. The method of claim 1 wherein the long acting formulation releases naltrexone for a period of at least two weeks.

4. The method of claim 1 wherein the long acting formulation releases naltrexone for a period of about four weeks.

5. The method of claim 1 wherein the long acting formulation is administered in a dose of about 380 mg of naltrexone wherein the serum AUC is about 3.3 times greater than that achieved by 50 mg/day oral administration.

6. The method of claim 1 wherein the long acting formulation is administered over a period of about 24 week period or longer.

7. The method of claim 1 further comprising a second administration of a long acting formulation comprising naltrexone at least about 7 days after the first administration.

8. The method of claim 7 wherein the second long acting formulation is substantially similar to the first long acting formulation.

9. The method of claim 7 wherein the second long acting formulation is the same as the first long acting formulation.

10. The method of claim 1 wherein the individual is an individual afflicted by alcohol dependency.

11. The method of claim 1 wherein the individual does not receive an initial oral dose of naltrexone.

12. The method of claim 1 wherein naltrexone is administered by injection.

13. The method of claim 1 wherein the naltrexone is present in the long acting formulation at a concentration of about 35% by weight.

14. A method for treating an individual in need of naltrexone comprising the step of parenterally administering a long acting formulation comprising about 190 mg to about 240 mg of naltrexone and a biocompatible polymer to the individual wherein the serum AUC of naltrexone is about two times greater than that achieved by 50 mg/day oral administration and wherein the biocompatible polymer is a polylactide-co-glycolide polymer.

15. The method of claim 14 wherein the long acting formulation is administered in a dose of about 190 mg of naltrexone.

* * * * *